United States Patent

Kim et al.

[11] Patent Number: 5,189,202
[45] Date of Patent: Feb. 23, 1993

[54] PROCESS FOR THE PREPARATION OF 3,3-DIMETHYL-4-PENTENOIC ACID

[75] Inventors: Yong Z. Kim; Won S. Kim, both of Daejeon-si, Rep. of Korea

[73] Assignee: Lucky, Ltd., Seoul, Rep. of Korea

[21] Appl. No.: 225,839

[22] Filed: Jul. 29, 1988

[30] Foreign Application Priority Data

Jul. 30, 1987 [KR] Rep. of Korea ............. 87-8318
Aug. 24, 1987 [KR] Rep. of Korea ............. 87-9244

[51] Int. Cl.$^5$ ............. C07C 67/30; C07C 57/02; C07C 57/18
[52] U.S. Cl. ............. 560/213; 562/598
[58] Field of Search ............. 562/598; 560/213

[56] References Cited

U.S. PATENT DOCUMENTS 4,214,097 7/1980 Kondo ............. 560/213
4,310,709 1/1982 Rebafka ............. 568/687

FOREIGN PATENT DOCUMENTS 2751766 5/1979 Fed. Rep. of Germany.

Primary Examiner—José G. Dees
Assistant Examiner—Joseph M. Conrad
Attorney, Agent, or Firm—Birch, Stewart, Kolasch & Birch

[57] ABSTRACT

In the present invention, 3,3-dimethyl-4-pentenoic acid (DPA) which is used for preparing permethric acid, an intemediate for preparing pyrethroid insecticides, is directly prepared from an isoprenol or a mixture of isoprenol and prenol without having to convert the isoprenol into a prenol or separate the mixture thereof into isoprenol and prenol. The present invention, therefore, has many advantages in view of yield, purity and procedure.

15 Claims, No Drawings

PROCESS FOR THE PREPARATION OF 3,3-DIMETHYL-4-PENTENOIC ACID

BACKGROUND OF THE INVENTION

The present invention relates to novel processes for the preparation of 3,3-dimethyl-4-pentenoic acid (hereinafter "DPA") represented by the formula (I).

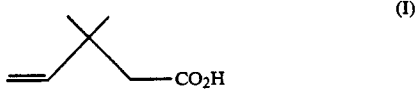
(I)

DPA of the formula (I) has been used for the preparation of permethric acid, an important intermediate for the preparation of pyrethroid insecticides. Various methods for preparing DPA are disclosed in JP patent laid open No. 77-42,853, No. 77-27,711, No. 76-131,819, No. 77-05,705 and No. 76-65,713. According to said inventions, DPA is prepared by hydrolysis of ethyl-3,3-dimethylpentenoate (hereinafter "EDP") which is synthesized by ether formation and Claisen rearrangement using 3-methyl-2-butene-1-ol (hereinafter "prenol") and triethylorthoacetate (hereinafter "TOA") in the presence of an acid catalyst, but said method is indicated as being undesirable because the prenol used therein can be prepared through only a very complicated procedure.

Some known methods for preparing prenol include for example, the first method German patent laid open No. 3021414, JP patent laid open No. 77-10207, and EP laid open No. 30109 disclosed a method for preparing prenol, in which isobutylene is reacted with formaldehyde, the obtained mixture is dehydrated to prepare isoprene, the isoprene is reacted with hydrochloric acid to form prenylchloride, the chlorine thereof is substituted for an acetyl group, and the resultant compound is converted into a prenol by deacetylation. The reaction formula of the above-mentioned method is as follows;

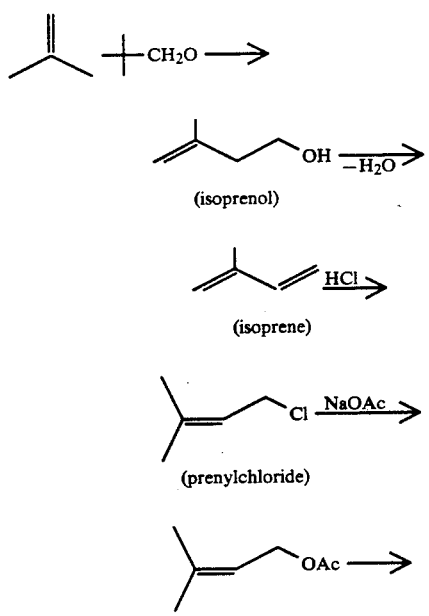

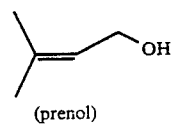
(prenol)

As a second method for preparing prenol, German patent laid open No. 2751766 disclosed another method, in which isoprenol is prepared as a mixture comprising 85% isoprenol and 5.9% prenol which is obtained by a reaction of isobutylene and formaldehyde under high temperature and pressure (Ref.: JP patent laid open No. 76-70,708), the resultant isoprenol is converted into prenol in the presence of a palladium catalyst to obtain a mixture of isoprenol and prenol having a ratio of 4:6, the mixture is fractionally distilled to separate prenol from it, and the residual isoprenol is converted into prenol by repeating the above process.

The steps of the above-mentioned process are represented as follows:

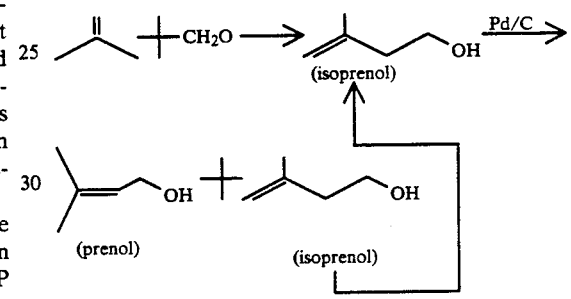

To obtain prenol, a starting material for the preparation of DPA, therefore, a multi-step process such as one of the foregoing must be carried out, and then there are many disadvantages in the procedure. Hereupon the present inventors expect that there will be many advantages in the process for preparing DPA, if DPA can be directly prepared from an isoprenol or a mixture of isoprenol and prenol.

SUMMARY OF THE INVENTION

The object of the present invention is to provide new methods for the preparation of DPA of good purity in high yield using an isoprenol or a mixture of isoprenol and prenol.

DETAILED DESCRIPTION OF THE INVENTION

The present invention is directed to a method for the preparation of DPA represented by the formula (I), which comprises reacting an isoprenol of the formula (II) with TOA of the formula (III) in the presence of an acid catalyst to obtain an ether of the formula (IV), converting the obtained ether into another ether of the formula (V) by reacting it in the presence of palladium and hydrogen and simultaneously undergoing a Claisen rearrangement to obtain a compound of the formula (VI), and hydrolyzing the obtained compound to prepare DPA of the formula (I).

(I)

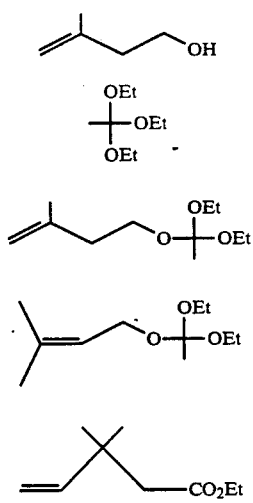

The acid catalysts of the present invention include, for example, phosphoric acid, methylacetic acid, p-toluenesufonic acid, benzoic acid, phenol and so on, and the amount thereof is preferably used in a range from 0.1 to 5% by mole based on TOA of the formula (III). In the case of using more than 5% by mole of the acid catalyst, an excess of by-product is undesirably produced.

Palladium, a catalyst which is used in the present invention, is preferably used in the form of palladium on charcoal (hereinafter "Pd/C"), the amount thereof is desirably used in a range from 0.1 to 5% by mole based on TOA of the formula (III).

The process for the preparation of DPA according to the present invention, may be carried out in the presence or absence of an organic solvent such as toluene, xylene and cymene, at a temperature of more than 0° C., preferably at room temperature or at the reflux temperature of the solvent.

And also, the present invention is directed to another method for preparation of DPA of the formula (I) using a mixture of isoprenol and prenol.

According to this method, a mixture of isoprenol and prenol in a ratio of from 9.5:0.5 to 4:6 is reacted with TOA of the formula (III) in the presence of hydrogen, palladium, selenium and acid catalysts to obtain an ester compound of the formula (VII), and the obtained compound is hydrolyzed to prepare DPA of the formula (I)

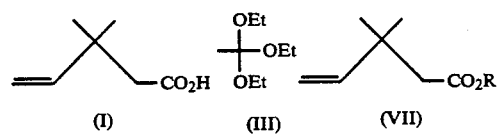

wherein R represents an ethyl, 3-methyl-3-butenyl or 3-methyl-2-butenyl group.

The acid catalysts of the present invention and the amount thereof are respectively the same as above.

The amount of said palladium catalyst is preferably used as a range from 0.1 to 10% by mole based on TOA of the formula (III), and on this occasion, palladium is used as the Pd/C form.

And, the amount of said selenium catalyst is desirably used as a range 0.1 to 20% by mole based on the amount of palladium catalyst. In the case that the amount of selenium exceeds the above-mentioned range, the action of palladium becomes undesirably weak and consequently the total progress of the reactions according to the present invention is delayed to a disadvantage.

The second method of the present invention may be also carried out in the presence or absence of an organic solvent such as toluene, xylene and cymene, at a temperature of more than 0° C., preferably at room temperature or at the reflux temperature of the solvent.

In the present invention, there is no need to convert isoprenol into prenol, and thus DPA can be directly prepared from isoprenol. And also, in the process for the preparation of DPA according to the present invention, the separation and purification steps of isoprenol and prenol from the mixture thereof are not required and DPA can be directly prepared from a mixture of isoprenol and prenol. Therefore, there are many advantages in yield, purity and process.

The present invention will be further described in detail with the examples given below. It should be noted that the invention is not limited to these examples.

In the following examples, the purity of the object compounds is determined using gas chromatography.

EXAMPLE 1

9.47 g (0.11 moles) of a mixture (9:1) of isoprenol and prenol, 16.22 g (0.1 moles) of TOA(triethylorthoacetate), 0.047 g of 10% Pd/C, 0.5 mg of selenium, and 0.047 g (0.001 moles) of phenol were added to 5 g of xylene in a flask equipped with a Perkin Triangle. After nitrogen and hydrogen gases were passed through for 20 minutes respectively, the reactor was filled with hydrogen gas.

The temperature of the reactor was raised to 120° C. and the ethanol produced was collected continuously for 2 hours.

The temperature was increased again to 145° C., and the resultant ethanol was collected continuously for 13 hours.

At the completion of the reaction, the reaction solution was cooled and filtered. 4 g of sodium hydroxide and 6 ml of water were added to the obtained filtrate and refluxed for 2 hours.

The resultant clear solution was washed with ether and the aqueous layer thereof was separated and acidified with 4N—HCl. As a result of the extraction with ether and distillation under reduced pressure, 11.30 g of the object product (yield 88.3%, purity 95.7%) was obtained.

EXAMPLES 2 TO 6

The procedures were the same as in Example 1 but mixtures of isoprenol and prenol having the composition ratios shown in Table 1 were used.

The results are shown in the following table.

TABLE 1

| Example No. | Composition Ratio | | Yield (%) | Purity (%) |
|---|---|---|---|---|
| | Isoprenol | Prenol | | |
| 2 | 8 | 2 | 89.1 | 96.0 |
| 3 | 7 | 3 | 90.4 | 96.2 |
| 4 | 6 | 4 | 92.8 | 95.8 |
| 5 | 5 | 5 | 93.0 | 96.0 |
| 6 | 4 | 6 | 94.5 | 97.0 |

EXAMPLE 7

9.47 g (0.11 moles) of a mixture (9:1) of isoprenol and prenol, 16.22 g (0.1 moles) of TOA, 0.047 g of 10% Pd/C, 0.5 mg of selenium, and 0.049 g (0.0005 moles) of phosphoric acid were added to 5 g of xylene in a flask equipped with a Perkin Triangle. After nitrogen and hydrogen gases were passed through for 20 minutes respectively, the reactor was filled with hydrogen gas.

Hereinafter the procedure was the same as in Example 1, and 11.24 g of the object product (yield 87.8%, purity 95.3%) was obtained.

EXAMPLES 8 TO 12

The procedures were the same as in Example 7 but using mixtures of isoprenol and prenol having the composition ratios shown in Table 2 were used.

The results are shown in the following table.

TABLE 2

| Example No. | Composition Ratio Isoprenol | Prenol | Yield (%) | Purity (%) |
|---|---|---|---|---|
| 8 | 8 | 2 | 88.4 | 95.8 |
| 9 | 7 | 3 | 89.0 | 95.9 |
| 10 | 6 | 4 | 90.1 | 96.0 |
| 11 | 5 | 5 | 92.3 | 96.0 |
| 12 | 4 | 6 | 93.4 | 96.2 |

EXAMPLE 13

9.47 g (0.11 moles) of a mixture (9:1) of isoprenol and prenol, 16.22 g (0.1 moles) of TOA, 0.047 g of 10% Pd/C, 0.5 mg of selenium, and 0.074 g (0.001 moles) of methylacetate were added to 5 g of xylene in a flask equipped with a Perkin Triangle. After nitrogen and hydrogen gases were passed through for 20 minutes respectively, the reactor was filled with hydrogen gas.

Hereinafter the procedure was the same as in Example 1, and 11.50 g of the object product (yield 89.8%, purity 95.4%) was obtained.

EXAMPLES 14 TO 18

The procedures were the same as in Example 13 but mixtures of isoprenol and prenol having the composition ratios shown in Table 3 were used.

The results are shown in the following table.

TABLE 3

| Example No. | Composition Ratio Isoprenol | Prenol | Yield (%) | Purity (%) |
|---|---|---|---|---|
| 14 | 8 | 2 | 90.0 | 95.8 |
| 15 | 7 | 3 | 91.2 | 95.5 |
| 16 | 6 | 4 | 92.0 | 94.8 |
| 17 | 5 | 5 | 91.5 | 95.6 |
| 18 | 4 | 6 | 92.4 | 95.8 |

EXAMPLE 19

9.47 g (0.11 moles) of a mixture (9:1) of isoprenol and prenol, 16.22 g (0.1 moles) of TOA, 0.047 g of 10% Pd/C, 0.5 mg of selenium, and 0.086 g (0.0005 moles) of p-toluenesulfonic acid were added to 5 g of xylene in a flask equipped with a Perkin Triangle. After nitrogen and hydrogen gases were passed through for 20 minutes respectively, the reactor was filled with hydrogen gas.

Hereinafter the procedure was the same as in Example 1, and 10.84 g of the object product (yield 84.7%, purity 96.5%) was obtained.

EXAMPLES 20 TO 24

The procedures were the same as in Example 19 but mixtures of isoprenol and prenol having the composition ratios shown in Table 4 were used.

The results are shown in the following table.

TABLE 4

| Example No. | Composition Ratio Isoprenol | Prenol | Yield (%) | Purity (%) |
|---|---|---|---|---|
| 20 | 8 | 2 | 87.8 | 95.4 |
| 21 | 7 | 3 | 89.0 | 95.0 |
| 22 | 6 | 4 | 92.4 | 95.1 |
| 23 | 5 | 5 | 90.8 | 94.5 |
| 24 | 4 | 6 | 92.5 | 96.3 |

EXAMPLE 25

9.47 g (0.11 moles) of a mixture (9:1) of isoprenol and prenol, 16.22 g (0.1 moles) of TOA, 0.047 g of 10% Pd/C, and 0.047 g (0.001 moles) of phenol were added to 5 g of xylene in a flask equipped with a Perkin Triangle and the reactor was filled with hydrogen gas.

Hereinafter the procedure was the same as in Example 1, but the ethanol, produced when the temperature is increased to 145° C., collection time is 10 hours instead of 13 hours, and 10.38 g of the object product (yield 85.0%, purity 95.0%) was obtained.

EXAMPLE 26

9.47 g (0.11 moles) of isoprenol, 16.22 g (0.1 moles) of TOA, 0.047 g of 10% Pd/C, and 0.049 g (0.0005 moles) of phosphoric acid were added to 5 g of xylene in a flask equipped with a Perkin Triangle, and the reactor was filled with hydrogen gas.

Hereinafter the procedure was the same as in Example 25, and 10.74 g of the object product (yield 83.9%, purity 95.0%) was obtained.

EXAMPLE 27

9.47 g (0.11 moles) of isoprenol, 16.22 g (0.1 moles) of TOA, 0.047 g of 10% Pd/C, and 0.074 g (0.001 moles) of methylacetate were added to 5 g of xylene in a flask equipped with a Perkin Triangle, and the reactor was filled with hydrogen gas.

Hereinafter the procedure was the same as in Example 25, and 10.77 g of the object product (yield 84.1%, purity 96.2%) was obtained.

EXAMPLE 28

9.47 g (0.11 moles) of isoprenol, 16.22 g (0.1 moles) of TOA, 0.047 g of 10% Pd/C, and 0.086 (0.0005 moles) of p-toluenesulfonic acid were added to 5 g of xylene, and the reactor was filled with hydrogen gas.

Hereinafter the procedure was the same as in Example 25, and 10.54 g of the object product (yield 82.3%, purity 95.7%) was obtained.

We claim:

1. A process for the preparation of 3,3-dimethyl-4-pentenoic acid (DPA) represented by the formula (I), which comprises reacting an isoprenol of the formula (II) with triethylorthoacetate (TOA) of the formula (III) in the presence of an acid catalyst to obtain an ether of the formula (IV), converting the obtained ether into another ether of the formula (V) by reacting it in the presence of palladium and hydrogen and simultaneously undergoing a Claisen rearrangement to obtain a compound of the formula (VI), and hydrolyzing the obtained compound (VI) to prepare DPA of the formula (I):

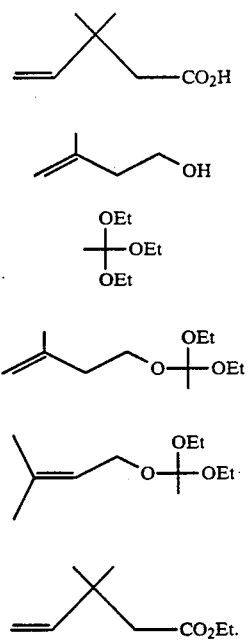

and hydrolyzing the obtained ester to prepare DPA of the formula (I):

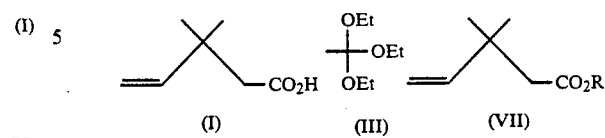

wherein R represents ethyl, 3-methyl-3-butenyl or 3-methyl-2-butenyl group.

2. The process as claimed in claim 1 wherein said acid catalyst is selected from the group consisting of phenol, benzoic acid, phosphoric acid, p-toluenesulfonic acid and methylacetic acid.

3. The process as claimed in claim 1 or 2 wherein the amount of the acid catalyst ranges from 0.1 to 5% by mole based on the TOA of the formula (III).

4. The process as claimed in claim 1 wherein the amount of said palladium ranges from 0.1 to 5% by mole based on the TOA of the formula (III).

5. A process for the preparation of 3,3-dimethyl-4-pentonic acid (DPA) represented by the formula (I), which comprises reacting a mixture of isoprenol and prenol having a ratio of from 9.5:0.5 to 4:6 with triethylorthoacetate (TOA) of the formula (III) in the presence of hydrogen, palladium, selenium and acid catalysts to obtain an ester compound of the formula (VII), 6. The process as claimed in claim 5 wherein said acid catalyst is selected from the group consisting of phenol, benzoic acid, phosphoric acid, p-toluenesulfonic acid and methylacetic acid.

7. The process as claimed in claim 5 or 6 wherein the amount of acid catalyst ranges from 0.1 to 5% by mole based on the TOA of the formula (III).

8. The process as claimed in claim 5 wherein the amount of said palladium ranges from 0.1 to 10% by mole based on the TOA of the formula (III).

9. The process as claimed in claim 5 wherein the amount of said selenium ranges from 0.1 to 20% by mole based on the amount of palladium.

10. The process as claimed in claim 2 wherein the amount of the acid catalyst ranges from 0.1 to 5% by mole based on the TOA of the formula (III), and wherein the amount of said palladium ranges from 0.1 to 5% by mole based on the TOA of the formula (III).

11. The process as claimed in claim 6 wherein the amount of acid catalyst ranges from 0.1 to 5% by mole based on the TOA of the formula (III), wherein the amount of said palladium ranges from 0.1 to 10% by mole based on the TOA of the formula (III), and wherein the amount of said selenium ranges from 0.1 to 20% by mole based on the amount of palladium.

12. The process as claimed in claim 1 wherein said process is carried out at room temperature.

13. The process as claimed in claim 1 wherein said process is carried out in the presence of an organic solvent at about the reflux temperature of the solvent.

14. The process as claimed in claim 5, wherein said process is carried out at room temperature.

15. The process as claimed in claim 5 wherein said process is carried out in the presence of an organic solvent at about the reflux temperature of the solvent.

* * * * *